(12) United States Patent
Richter

(10) Patent No.: US 7,048,714 B2
(45) Date of Patent: May 23, 2006

(54) DRUG ELUTING MEDICAL DEVICE WITH AN EXPANDABLE PORTION FOR DRUG RELEASE

(75) Inventor: Jacob Richter, Ramat Hasharon (IL)

(73) Assignee: BIOrest Ltd., Tel Aviv (IL)

( * ) Notice: Subject to any disclaimer, the term of this patent is extended or adjusted under 35 U.S.C. 154(b) by 0 days.

(21) Appl. No.: 10/283,684

(22) Filed: Oct. 30, 2002

(65) Prior Publication Data

US 2004/0087902 A1   May 6, 2004

(51) Int. Cl.
  *A61M 25/10*  (2006.01)
(52) U.S. Cl. .............. 604/103.02; 604/96.01; 604/103.01; 604/509
(58) Field of Classification Search .......... 604/103.01, 604/103.06, 103.02, 509, 508, 96.01, 500
  See application file for complete search history.

(56) References Cited

U.S. PATENT DOCUMENTS

| | | | |
|---|---|---|---|
| 5,049,132 A | 9/1991 | Shaffer et al. | |
| 5,102,402 A * | 4/1992 | Dror et al. ................... | 604/265 |
| 5,112,305 A | 5/1992 | Barath | |
| 5,242,397 A | 9/1993 | Barath | |
| 5,295,962 A | 3/1994 | Crocker et al. | |
| 5,324,261 A | 6/1994 | Amundson et al. | |
| 5,458,568 A | 10/1995 | Racchini et al. | |
| 5,498,238 A * | 3/1996 | Shapland et al. ............. | 604/501 |
| 5,569,184 A * | 10/1996 | Crocker et al. .............. | 604/509 |
| 5,628,730 A | 5/1997 | Shapland et al. | |
| 5,674,192 A | 10/1997 | Sahatjian et al. | |
| 5,709,653 A | 1/1998 | Leone | |
| 5,713,860 A * | 2/1998 | Kaplan et al. .......... | 604/103.01 |
| 5,792,105 A * | 8/1998 | Lin et al. ................ | 604/103.01 |
| 5,800,392 A | 9/1998 | Racchini | |
| 5,843,033 A | 12/1998 | Ropiak | |
| 6,048,332 A | 4/2000 | Duffy et al. | |
| 6,129,705 A * | 10/2000 | Grantz ................... | 604/103.02 |
| 6,146,358 A | 11/2000 | Rowe | |
| 6,200,257 B1 | 3/2001 | Winkler | |
| 6,280,411 B1 | 8/2001 | Lennox | |
| 6,364,856 B1 * | 4/2002 | Ding et al. ............. | 604/103.02 |
| 6,409,716 B1 | 6/2002 | Sahatjian et al. | |
| 6,419,692 B1 | 7/2002 | Yang et al. | |
| 6,544,221 B1 * | 4/2003 | Kokish et al. ......... | 604/103.01 |
| 6,585,764 B1 | 7/2003 | Wright et al. | |
| 6,629,969 B1 * | 10/2003 | Chan et al. .................. | 604/508 |
| 2001/0001816 A1 * | 5/2001 | Feiring ...................... | 604/509 |
| 2002/0082552 A1 | 6/2002 | Ding et al. | |

OTHER PUBLICATIONS

Veith, F.J. et al., *Journal of Vascular Surgery*. 1995, 21: 670-85.
Markou, C.P. et al., *Journal of Controlled Release*. 1998, 53: 281-288.

* cited by examiner

*Primary Examiner*—Nicholas D. Lucchesi
*Assistant Examiner*—Melissa A. McCorkle
(74) *Attorney, Agent, or Firm*—Morgan & Finnegan LLP

(57) ABSTRACT

The present invention relates to a medical device and a method of delivering a drug to a target circulation or tissue. The medical device has an expandable portion which is fabricated from a porous elastomeric material with a plurality of voids therein. The voids are loaded with drugs in various formulations. Upon inflation of the expandable portion, the overall diameter increases, the wall thickness decreases and, consequently, the voids are stretched to cause the drug to be expelled from the voids and into the bodily lumen or tissue adjacent to the medical device. The voids include any open volume within the expandable portion capable of containing the drug.

30 Claims, 3 Drawing Sheets

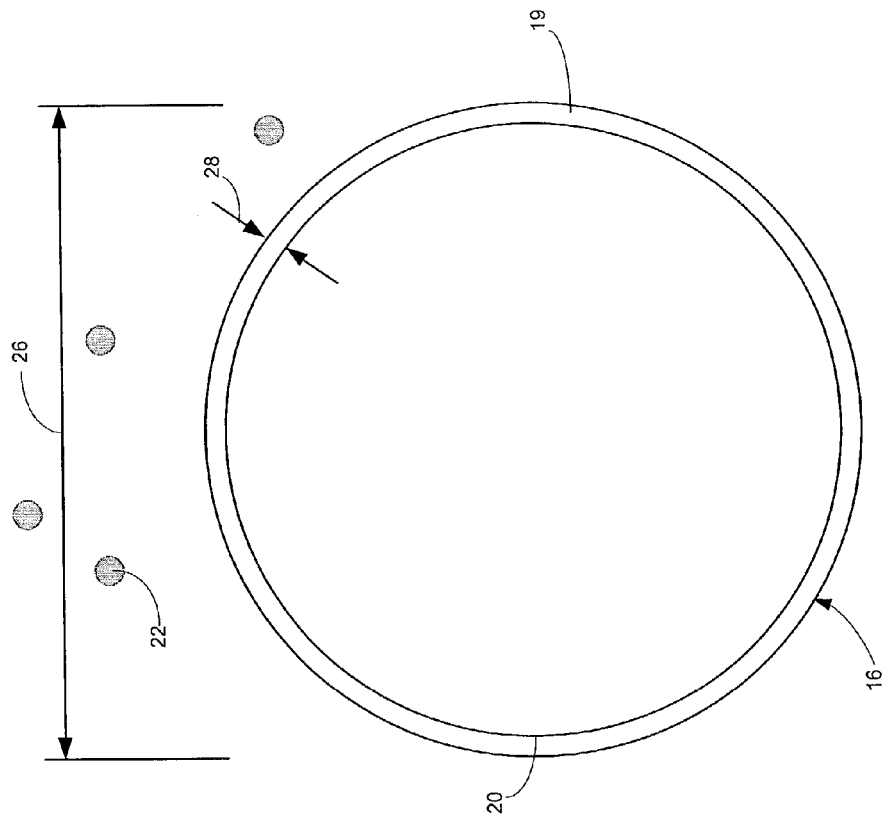
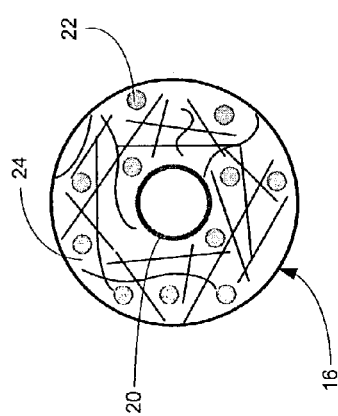
FIG. 5
FIG. 4

DRUG ELUTING MEDICAL DEVICE WITH AN EXPANDABLE PORTION FOR DRUG RELEASE

FIELD OF THE INVENTION

The present invention relates to medical devices for delivering drugs to an internal tissue or lumen of a patient.

BACKGROUND OF THE INVENTION

Various methods are presently known in the art for the delivery of a pharmaceutical composition to treat various medical conditions. The pharmaceutical composition may be provided to a human or veterinary patient in need of therapeutic treatment by a variety of routes such as, for example, subcutaneous, topical, oral, intraperitoneal, intradermal, intravenous, intranasal, rectal, intramuscular, and within the pleural cavity. Administration of pharmaceutical compositions is usually accomplished orally or parenterally. However, it has become increasingly common to treat a variety of medical conditions by introducing an implantable medical device partly or completely into the esophagus, trachea, colon, biliary tract, urinary tract, vascular system or other location within a human or veterinary patient. For example, many treatments of the vascular system entail the introduction of a device such as a stent, catheter, balloon, guide wire, cannula or the like into the body.

Exposure, however, to a medical device which is implanted or inserted into the body of a patient can cause the body tissue to exhibit adverse physiological reactions. These adverse reactions can occur whether the medical device is introduced by a major surgical procedure or by a minimally invasive technique; they include, for example, the formation of emboli or clots, cell proliferation, occlusion of blood vessels, platelet aggregation, or calcification. To reduce the potential occurrence of such adverse effects associated with implanted medical devices, pharmaceuticals, such as anticoagulants and antiproliferation drugs, have been administered in or on such medical devices.

In addition to administering drugs to treat and/or prevent the adverse reactions to inserted or implanted medical devices, such devices can also be used for the improved localized delivery of drugs to diseased tissues or body lumens in most branches of medicine and for most types of drugs. Such drugs include, for example, antibiotics, anti-inflammatory agents, anti-cancer agents and genetic material for gene therapy. Thus, the medical device enables drugs to be administered locally rather than systemically.

Methods for delivering drugs to body lumens or tissues may involve, for example, the use of catheters having a balloon disposed on the distal end of the catheter, with the drugs coated on the balloon surface. For instance, U.S. Pat. No. 5,102,402 to Dror et al. and U.S. Pat. No. 6,146,358 to Rowe describe medical devices, typically a balloon catheter, in which the exterior surface of the balloon is coated with drugs. Generally, the drugs are applied to the surface of the balloon by known coating methods, including spraying, dipping, rolling, brushing, solvent bonding, adhesives, or welding. The drug is delivered to the target lumen or tissue by inserting the catheter into the body lumen and maneuvering it through the cardiovascular system to the target site. Once in the proper position, the balloon is inflated for contacting the afflicted tissue so that the drug is released and retained in the lumen or tissue as the balloon is deflated.

Rather then being coated directly on the balloon surface, as described supra, the drug may be embedded in a separate polymer layer, which is then coated or otherwise applied to the balloon surface. For instance, U.S. Pat. No. 6,409,716 to Sahatjian et al. and U.S. Pat. No. 6,364,856 to Ding et al. disclose balloon catheters with drug-embedded polymer layers coated upon the balloon surface. These medical devices allow for a rapid release of the drug from the coated polymer layer during compression of the polymer coating against the wall of the lumen as the balloon is expanded. Sahatjian et al. '716 describes a balloon catheter with a swellable hydrogel polymer layer adhered to the surface of the balloon, whereas Ding et al. '856 discloses a balloon catheter with a sponge non-hydrogel polymer coating applied to the surface of the balloon.

Drug-coated medical devices of the foregoing types do, however, have certain disadvantages. For example, the application of a separate coating (either of the drug itself or of a drug-containing layer) to the balloon surface usually involves multiple steps. The coating may not adhere properly to the balloon surface, thereby causing difficulties when using the device. For example, inserting or implanting the medical device may be difficult if the coating is not properly adhered to the balloon surface. In addition, the effectiveness of the drug application may be hampered if the coating has been compromised.

Hence, there is a need for a device which reliably delivers drugs, therapeutic agents, or bioactive materials directly into a localized tissue area so as to treat and/or prevent conditions and diseases.

SUMMARY OF THE INVENTION

The above-identified disadvantages are addressed and a technical advance is achieved by the drug eluting medical device of the present invention having an expandable portion made of a porous elastomeric material. The expandable portion is made of an elastomeric polymer and provided with a plurality of voids. The voids of the expandable portion are infused with therapeutic drugs or reagents, including without limitation, medicines, adjuvants, proteins, lipids and other compounds which treat the tissue or circulation and/or ameliorate any malady in the vicinity of the device. The drug may be present in various formulations including, but not limited to, free molecules, aggregates, flocculates, or particles containing the drugs. For example, the drug may be encapsulated in particles or controlled release carriers such as liposomes, microparticles and nanoparticles.

In practice of the invention, the medical device (with its expandable portion) is configured for insertion into the body and contact with a tissue or lumen. Once the expandable portion reaches its target area, it is inflated under controlled pressure in order to expand the target portion of the body lumen, or to otherwise press against the target tissue. As the expandable portion is inflated, it stretches and increases in diameter, while the thickness of the wall of the expandable portion decreases. Upon inflation of the expandable portion, the voids which contain the drug are also stretched and, as a result, cause the drug to be expelled from the voids.

In one preferred embodiment of the invention, the medical device is a balloon catheter, and the expandable portion is a balloon made of a porous elastomeric material. For example, the balloon can be fabricated entirely of an elastomeric material with a plurality of voids therein. It is preferable that the drug-containing voids are separated from the interior space of the expandable portion. This may be effected by, for example, sealing the interior surface of the expandable portion or otherwise rendering it impermeable.

According to another aspect of the invention, a method of delivering a drug to a tissue or circulation includes inserting a medical device with an expandable portion made of a porous elastomeric material having voids therein. The voids are infused with a drug that is expelled into the lumen of a body upon inflation of the expandable portion.

The advantages of this invention, both as to its construction and mode of use, will be readily appreciated as the same becomes better understood by reference to the following detailed description when considered in connection with the accompanying drawings.

BRIEF DESCRIPTION OF THE DRAWINGS

FIG. 4 is a cross-sectional view of an expandable catheter in accordance with another embodiment of the present invention.

FIG. 5 is a cross-sectional view of an expandable catheter in its expanded state in accordance with another embodiment of the present invention.

DETAILED DESCRIPTION OF THE INVENTION

Figure 1:
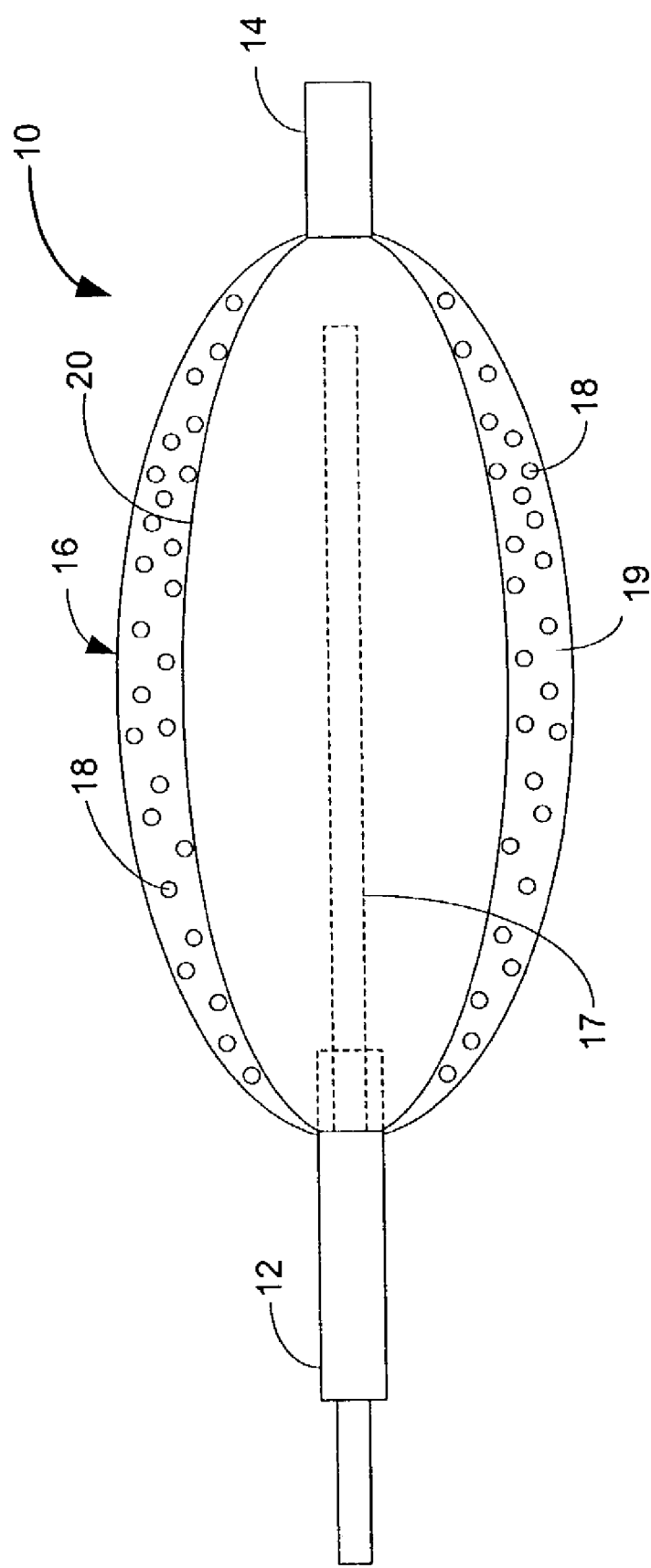
FIG. 1 illustrates an expandable catheter in accordance with an embodiment of the present invention.

The medical device of the present invention includes any one of a number of medical devices that can be adapted for the localized delivery of drugs or therapeutic agents within the body. FIG. 1 is a perspective view of one example of a medical device applicable to the present invention. In this embodiment, the medical device comprises an expandable catheter (10) having proximal (12) and distal (14) ends. Mounted towards the distal (14) end of the catheter (10) is an expandable portion (16). The expandable portion (16) is a balloon, and more preferably, a perfusion balloon, as known in the art. The expandable balloon portion (16) is connected to an inflation-lumen (17) which can fill the balloon with fluid, such as a liquid or pressurized gas, thus expanding the balloon. However, it shall be understood that additional devices and methods known in the art may also be used to inflate the expandable portion. During an angioplasty procedure, for example, the expanded balloon contacts the walls of a bodily lumen to expand the bodily lumen and thereby relieve stenosis.

Figure 3:
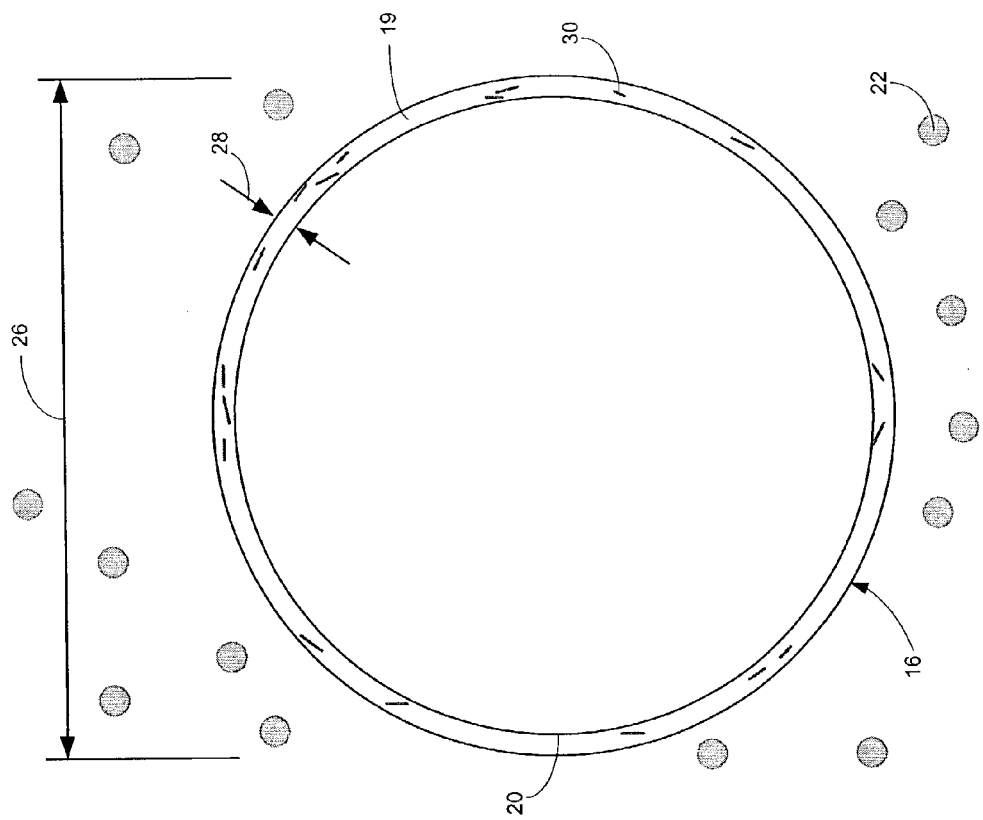
FIG. 3 is a cross-sectional view of an expandable catheter in its expanded state in accordance with an embodiment of the present invention.
Figure 2:
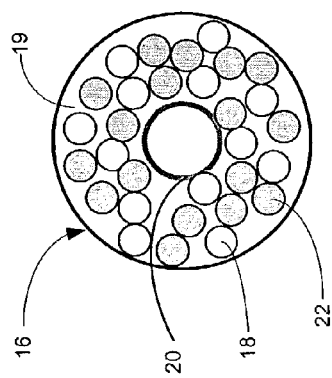
FIG. 2 is a cross-sectional view of an expandable catheter in accordance with an embodiment of the present invention.

Referring to FIGS. 1 through 3, the balloon or expandable portion (16) is made of a porous elastomeric material having a plurality of voids (18) therein. Here, the expandable portion (16) is annular in shape with a wall (19) of predetermined thickness and with the voids distributed, as desired, throughout the balloon wall (19). Advantageously, the inner boundary (20) of the expandable portion (16) may be sealed or otherwise rendered impermeable, thus allowing the balloon to be expanded by the addition of liquid or pressurized gas without allowing the drug to penetrate the interior of the balloon. The impermeable boundary (20) similarly prevents the liquid or pressurized gas from entering the voids (18) of the porous material.

As illustrated in FIG. 2, the entire cross-section of the expandable portion (16) contains a plurality of voids (18). The voids include any open volume within the walls of the expandable portion, such as, for example pores, apertures, and spaces. The voids are characterized by any open volume that may be impregnated with a therapeutic drug or reagent (22). As shown in FIGS. 1 and 2, the voids may comprise pores (18) within the wall (19) of the expandable portion (16). The voids (18) need not, however, be uniform in size or volume and, as such, may contain different volumetric amounts of therapeutic drug or reagent (22).

In use, and according to the methodology of the present invention, upon inflation of the expandable portion, the porous elastomeric material stretches so that the thickness (28) of wall (19) decreases, i.e., the wall (19) becomes thinner, as the overall diameter (26) of the expandable portion (16) increases, as illustrated in FIG. 3. During the inflation of the expandable portion (16) and the subsequent stretching of the porous material, the embedded voids (18) are also stretched to cause the drug to be expelled from the voids and into the bodily lumen or tissue adjacent to the catheter. Thus, for example, as best illustrated in FIG. 3, the voids (18) are stretched and may ultimately become slits (30). In essence, the drug is "squeezed" out of the voids, and released into the bodily lumen or into the tissue surrounding the expandable portion.

In a further embodiment of the present invention, the voids may be open spaces between fibers in the matrix of the expandable portion. As shown in FIGS. 4 and 5 the expandable portion (16) contains open spaces (24) dispersed throughout its entire cross-section. The open spaces (24) may be infused with a therapeutic drug or reagent (22). As described above, upon inflation of the expandable portion (16) the elastomeric material is stretched, and, the thickness (28) of the wall (19) of the expandable portion (16) decreases. In addition, the open spaces (24) between the fibers become compressed to cause the drug (22) to be expelled from the open spaces and into the bodily lumen or tissue adjacent to the catheter.

It will be understood by those skilled in the art, in view of the foregoing description, that the medical device of the invention can be constructed so that the drug embedded in the voids of the expandable portion is released into the bodily lumen surrounding the device when pressure is applied by inflation of the expandable portion, but before the expandable portion contacts a tissue or the walls of that lumen. The medical device, however, may also be designed so that the drug is released when the expandable portion contacts the wall of the bodily lumen and the pressure created by the expandable portion against the tissue compresses the expandable portion and the drug is expelled from the voids into the lumen. In short, the expandable portion may be configured to expel the drugs prior to contacting the wall of a bodily lumen or tissue or after the point of contact.

It will also be understood that the expandable portion (16) can similarly be adapted to provide the appropriate amount of drug to the target site. Thus, administration of the drug according to the invention enables the drug to be site-specific, such that the release of high concentrations and/or high potency drugs may be limited to the immediate area of the diseased tissue. Furthermore, use of an expandable portion made of a porous elastomeric material allows the drug to be administered to the diseased tissue without injuring surrounding healthy tissue. In the case of an angioplasty procedure, the introduction of the drug into the lumen wall occurs simultaneously with the opening of the occlusion by the dilation balloon. Thus, as cracking of the plaque is caused by dilation, a drug or reagent can be applied to the affected area to counteract the effects of the trauma and/or facilitate amelioration of the occlusion.

It will also be understood that the elastomeric and porous material of the invention is preferably selected such that the drug is not prematurely released prior to inflation of the expandable portion at the target circulation or tissue. The material should be biostable, biocompatible and inert to the anticipated drug or reagent. Indeed, it is preferred that the material of the expandable portion is elastomeric. For example, the material may be an elastomeric polymer. Examples of such elastomeric polymers include without limitation, silicones, polyurethanes, polyisobutylene and its copolymers, polyolefin elastomers, ethylene vinyl acetate copolymers, and thermoplastic elastomers. In addition, the material may also comprise elastomeric fibers or filaments. However, the invention is not limited to any particular material.

Although the expandable portion can be formed by using a single type of polymer, any combination of polymers can be employed. Additives may also be joined with various porous polymers to increase the elasticity or other desired characteristic of the polymer.

The thickness of the expandable portion can vary depending on the application, i.e., the target tissue or circulation. The selected thickness of the expandable portion can also depend upon the dosage to be delivered to the site, the size of the site into which it is to be delivered, and the type of drug.

It will also be understood that any method known to those skilled in the art may be used to infuse or fill the voids of the expandable portion with a drug or reagent. For example, in one method the drug may be dissolved or dispersed within a solvent and the expandable portion immersed into the drug solution. As another alternative, the drug may be loaded into the voids of the expandable portion during manufacture of the medical device, or, the drug may be loaded just prior to the insertion or implantation procedure.

An additional example of infusing the voids of the expandable portion includes spraying, dipping, rolling or brushing the drug into the porous elastomeric material of the expandable portion. After adsorption of the drug into the voids of the expandable portion, the medical device is ready for use. As yet another approach, a mixture of the polymeric materials and drug formulations can be prepared and then formed into the expandable portion.

The dosage applied to the tissue may be controlled by regulating the concentration of the drug in the solution applied to the expandable portion. The dosage may also be controlled by regulating the time the solution is in contact with the expandable portion; thus, controlling the amount of drug that diffuses or is adsorbed into the voids. Other factors affecting the dosage of the drug include without limitation, the ability of the expandable portion to release the drug, which is determined by, for example, the wall thickness of the expandable portion, its surface area, its resiliency, the ratio of the void volume to the total volume of the expandable portion and the void characteristics. Furthermore, the compression ratio of the expandable portion during inflation will also affect the amount of drug that is released from the voids.

The drugs or reagents to be loaded into the voids of the expandable portion may comprise any suitable formulation. For example, the drugs may be formulated as free molecules, aggregates or as a composite, wherein the drugs are mixed with other reagents. The drugs may also be encapsulated within drug release particles such as, for example, liposomes. The particles may also include inert polymeric particles, such as microparticles, nanoparticles, microcapsules or nanocapsules. Alternatively, the particles may comprise biologically derived reagents, such as lipids, sugars, carbohydrates, proteins, nucleic acids, and the like. Specifically, such particles can be release carriers which provide an effective release of the therapeutic agent to the target tissue or cells.

Any type of drug or therapeutic reagent that may be delivered in a localized manner may be used in the present invention. Such drugs include without limitation, anti-spasmodic, anti-thrombogenic, anti-platelet agents, antibiotics, steroids, antioxidants, anticancer agents, anti-inflammatory agents, chemotherapeutic agents, anti-coagulant agents, or any suitable combination thereof. Also, genetic material such as genes or nucleic acids, may also be embedded in the voids of the expandable portion. Such genetic material is usually packaged in particles or release carriers as discussed supra.

As another example, the drug embedded within the voids of the expandable portion is used for reducing, delaying or eliminating restenosis following angioplasty. Reducing restenosis includes decreasing the thickening of the inner blood vessel lining that results from stimulation of smooth muscle cell proliferation following angioplasty. Delaying restenosis includes delaying the time until onset of visible hyperplasia following angioplasty, and eliminating restenosis following angioplasty includes completely reducing and/or completely delaying hyperplasia to an extent which makes it no longer necessary to intervene. Methods of intervening include reestablishing a suitable blood flow through the vessel by methods such as, for example, repeat angioplasty and/or stent placement.

The present invention may also be utilized for vascular as well as non-vascular applications. For example, the medical device may target the lumen of any circulation or may be readily introduced into solid tissue mass by percutaneous techniques. The expandable portion can then be inflated to expel the drug from the interior of the void into the solid tissue mass.

Optionally, it may desirable to position a protective layer over the expandable portion to prevent premature release of the drug from the voids of the expandable portion before the medical device has reached its target circulation or tissue. If utilized, the protective layer is preferably biodegradable and slowly consumed during the insertion or deployment of the medical device. The thickness and type of material used to construct the protective layer is selected based on the type of device, the insertion or deployment method used, and the length of time the medical device is in contact with body fluids prior to reaching its target tissue or circulation.

It is to be understood that the embodiments and variations shown and described herein are merely illustrative of the principles of the present invention. Therefore, various adaptations and modifications may be implemented by those skilled in the art without departing from the spirit and scope of the present invention.

I claim:

1. A medical device for delivering a drug to a tissue or circulation, comprising:
   a) an expandable balloon consisting essentially of a single generally porous elastomeric material having a plurality of voids therein, said voids comprise locations of open volume inside the porous elastomeric material of the balloon; and
   b) at least one drug pre-loaded inside the voids inside generally porous elastomeric material of the balloon, wherein the expandable balloon can be inflated and the voids stretched for expelling the drug from the voids.

2. The medical device of claim 1, wherein an inner boundary of the expandable balloon is substantially impermeable.

3. The medical device of claim 1 wherein the voids are pores.

4. The medical device of claim 1, wherein the voids are spaces between fibers in a matrix of the expandable balloon.

5. The medical device of claim 1, wherein the drug is encapsulated in a particle.

6. The medical device of claim 1, wherein the drug is in aggregates.

7. The medical device of claim 1, wherein at least two voids in the wall structure of the expandable balloon are different volumes.

8. The medical device of claim 1, wherein the expandable balloon is annular shaped.

9. The medical device of claim 1, wherein the drug is an anti-proliferative agent.

10. The medical device of claim 1, wherein the drug is a chemotherapeutic agent.

11. The medical device of claim 1, wherein the drug is an antibiotic.

12. The medical device of claim 1, wherein the drug is genetic material.

13. The medical device of claim 1, wherein the drug is expelled from the voids in the porous elastomeric material of the expandable balloon when the expandable balloon is inflated and contacts a tissue or a wall of a bodily lumen.

14. The medical device of claim 1, wherein the drug is expelled from the voids in the porous elastomeric material of the expandable balloon when pressure is applied to the voids by inflation of the expandable balloon and before the expandable balloon contacts a tissue or a wall of a bodily lumen.

15. The medical device of claim 1, further comprising a protective layer over the expandable balloon to prevent premature release of the drug from the voids in the single wall structure of the expandable balloon.

16. The medical device of claim 15, wherein the protective layer is biodegradable.

17. A method of delivering a drug to a tissue or circulation, comprising:
 a) providing a medical device with an expandable balloon consisting essentially of a single generally porous elastomeric material having a plurality of voids therein, said voids comprise locations of open volume inside the porous elastomeric material of the expandable balloon that are pre-loaded with at least one drug;
 b) positioning the medical device at the tissue or in circulation;
 c) inflating the expandable balloon so that the voids are stretched; and
 d) expelling the drug from the voids in the generally porous elastomeric material of the balloon into the area surrounding the tissue or in circulation, thereby delivering an effective amount of the drug.

18. The method of claim 17, wherein an inner boundary of the expandable balloon is substantially impermeable.

19. The method of claim 17, wherein the voids are pores.

20. The method of claim 17, wherein the voids are spaces between fibers in a matrix of the expandable balloon.

21. The method of claim 17, wherein the drug is encapsulated in a particle.

22. The method of claim 17, further comprising controlling the dosage delivered to the tissue or in circulation.

23. The method of claim 17, wherein the drug is an anti-proliferative agent.

24. The method of claim 17, wherein the drug is a chemotherapeutic agent.

25. The method of claim 17, wherein the drug is an antibiotic.

26. The method of claim 17, wherein the drug is genetic material.

27. The method of claim 17, wherein the drug is expelled from the voids in the porous elastomeric material of the expandable balloon when the expandable balloon is inflated and contacts a tissue or a wall of a bodily lumen.

28. The method of claim 17, wherein the drug is expelled from the voids in the porous elastomeric material of the expandable balloon when pressure is applied to the voids by inflation of the expandable balloon and before the expandable balloon contacts a tissue or a wall of a bodily lumen.

29. The method of claim 17, wherein the medical device further comprising a protective layer over the expandable balloon to prevent premature release of the drug from the voids in the wall structure of the expandable balloon.

30. The method of claim 29, wherein the protective layer is biodegradable.

* * * * *